(12) United States Patent
Yung et al.

(10) Patent No.: US 9,694,350 B2
(45) Date of Patent: Jul. 4, 2017

(54) METHODS AND CATALYSTS FOR GREEN BIODIESEL PRODUCTION FROM UNREFINED LOW GRADE FEEDSTOCK

(71) Applicant: The Hong Kong Polytechnic University, Hong Kong (CN)

(72) Inventors: Ka Fu Yung, Hong Kong (CN); Wing Tak Wong, Hong Kong (CN); Tsz Lung Kwong, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 0 days.

(21) Appl. No.: 15/078,558

(22) Filed: Mar. 23, 2016

(65) Prior Publication Data

US 2016/0279616 A1    Sep. 29, 2016

Related U.S. Application Data

(60) Provisional application No. 62/138,963, filed on Mar. 26, 2015.

(51) Int. Cl.
*C10L 1/02*        (2006.01)
*B01J 35/02*      (2006.01)
(Continued)

(52) U.S. Cl.
CPC .............. *B01J 23/80* (2013.01); *B01J 23/005* (2013.01); *B01J 35/026* (2013.01); *B01J 35/1042* (2013.01); *B01J 35/1057* (2013.01); *B01J 37/0018* (2013.01); *B01J 37/086* (2013.01); *C01G 49/0063* (2013.01); *C07C 67/02* (2013.01); *C07C 67/03* (2013.01); *C10L 1/026* (2013.01); *C11C 3/003* (2013.01); *B01J 35/002* (2013.01); *B01J 35/023* (2013.01); *B01J 35/1014* (2013.01); *B01J 35/1038* (2013.01); *B01J 35/1061* (2013.01); *C01P 2002/32* (2013.01); *C01P 2002/72* (2013.01);
(Continued)

(58) Field of Classification Search
CPC combination set(s) only.
See application file for complete search history.

(56) References Cited

U.S. PATENT DOCUMENTS

| 5,908,946 A | 6/1999 | Stern |
|---|---|---|
| 8,163,946 B2 | 4/2012 | Yan |

(Continued)

FOREIGN PATENT DOCUMENTS

CN          101811055          8/2010

OTHER PUBLICATIONS

P. S. Sreeprasanth et al, 2006, "Hydrophobic, solid acid catalysts for production of biofuels and lubricants", Applied Catalysis A: General, 314, 148-159.

(Continued)

*Primary Examiner* — Ellen McAvoy
*Assistant Examiner* — Chantel Graham
(74) *Attorney, Agent, or Firm* — Law Offices of Albert Wai-Kit Chan, PLLC

(57) ABSTRACT

This invention provides a catalyst comprising a new form of $ZnFe_2O_4$ spinel nanoparticles, and a method for preparing same. The catalyst is useful for catalyzing the esterification of fatty acids or transesterification of triglycerides, wherein the reaction rate and conversion can be enhanced by free fatty acids.

20 Claims, 13 Drawing Sheets

(51) Int. Cl.
*C07C 67/02* (2006.01)
*C01G 49/00* (2006.01)
*B01J 35/10* (2006.01)
*B01J 23/80* (2006.01)
*B01J 37/08* (2006.01)
*C07C 67/03* (2006.01)
*C11C 3/00* (2006.01)
*B01J 23/00* (2006.01)
*B01J 37/00* (2006.01)
*B01J 35/00* (2006.01)

(52) U.S. Cl.
CPC ...... *C01P 2002/77* (2013.01); *C01P 2002/82* (2013.01); *C01P 2002/85* (2013.01); *C01P 2004/03* (2013.01); *C01P 2004/04* (2013.01); *C01P 2004/64* (2013.01); *C01P 2006/12* (2013.01); *C01P 2006/14* (2013.01); *C01P 2006/16* (2013.01); *C01P 2006/17* (2013.01); *C10L 2200/0476* (2013.01); *C10L 2270/026* (2013.01); *Y02E 50/13* (2013.01)

(56) References Cited

U.S. PATENT DOCUMENTS 8,513,479 B2 * 8/2013 Chung .................. B01J 23/002
  502/329
8,551,443 B2 * 10/2013 Mamedov ................ B01J 23/80
  423/594.1

OTHER PUBLICATIONS

F. Yan et al, 2011, "Fe—Zn double-metal cyanide complexes catalyzed biodiesel production from high-acid-value oil", Renewable Energy, 36, 2026-2031.

K. Thirunavukkarasu et al, 2014, "The role of surface Zn2+ ions in the transesterification of vegetable oils over ZnO supported on Al2O3 supported on Al2O3 and Fe2O3", Catalysis Science & Technology, 4, 851-860.

T. M. Sankaranarayanan et al, 2013, "Catalytic properties of spinel-type mixed oxides in transesterification of vegetable oils", J. Mol. Catal. A: Chem., 379, 234-242.

* cited by examiner

METHODS AND CATALYSTS FOR GREEN BIODIESEL PRODUCTION FROM UNREFINED LOW GRADE FEEDSTOCK

FIELD OF THE INVENTION

This invention relates to biodiesel production, particularly, the methods and catalysts for biodiesel production from low grade feedstock.

BACKGROUND OF THE INVENTION

Biodiesel is a non-toxic, carbon neutral renewable fuel which is generally produced by transesterification of oil feedstock with short chain alcohols and exhibits similar physical and chemical properties to conventional diesel fuel. Biodiesel may curtail the harmful emissions such as NOx, SOx, CO, $CO_2$, unburnt hydrocarbon and particulates.

The conventional production of biodiesel through transesterification involves the breaking down of triglyceride molecule with alcohols to yield biodiesel and glycerol with presence of catalyst. Conventional production of biodiesel often involves a homogeneous strong acid (e.g. HCl or $H_2SO_4$) or strong base (e.g. KOH or NaOH).

The production cost for the transesterification of refined plant oil is 1.5 times higher than that of the conventional diesel fuel. It is advantageous that the development of biodiesel production from waste oil or low grade feedstock through transesterification directly would reduce the production cost. The waste oil and low grade feedstock often contain high degree of free fatty acids (FFAs) and water content which hinder the transesterification process. The high water content in low grade feedstock may result in hydrolysis of triglyceride to produce FFAs while the FFAs would subsequently react with the base catalyst to yield soaps that complicate the separation of glycerol from the catalytic system and thus, it suppresses the transesterification reaction.

To overcome this issue, two-step biodiesel production is applied to the low grade feedstock or waste oil. The first step of the two-step operation involves the pre-treatment step of FFAs removal by an acidic catalyst (e.g. HCl or $H_2SO_4$) followed by a second step of alkaline (e.g. KOH or NaOH) catalyzed transesterification. These homogeneous strong acid and base are highly corrosive and require a large amount of fresh water for biodiesel purification to generate an enormous amount of waste water and thus, the production cost would be increased. Although this two-step operation may utilize the low grade feedstock and waste oil, the process requires multi-steps washing and leads to loss of catalyst. The development of a new class of heterogeneous catalyst system that are active in one-step simultaneous esterification and transesterification is beneficial to increase the flexibility for various low grade feedstock selected in biodiesel production and reduce production cost.

SUMMARY OF THE INVENTION

In one embodiment, this invention provides a durable bimetallic catalyst for green biodiesel production from low grade feedstock through one-step simultaneous esterification and transesterification reaction with no washing required.

In one embodiment, this invention provides a catalyst for catalyzing the esterification of fatty acids or transesterification of triglycerides, comprising $ZnFe_2O_4$ spinel nanoparticles.

In one embodiment, this invention provides a method for transesterification, comprising the steps of: providing a catalyst comprising $ZnFe_2O_4$; contacting said catalyst with one or more alcohols and a composition comprising one or more esters to form a reaction mixture; and heating said reaction mixture to form transesterification products.

In one embodiment, this invention further provides a method for preparing a $ZnFe_2O_4$ catalyst, comprising the steps of: a) preparing a first solution by dissolving ethylenediaminetetraacetic acid (EDTA) in purified water, followed by adding a base until the pH is 3 to 10; b) preparing a second solution by dissolving a surfactant in purified water; c) adding the second solution dropwise to the first solution; d) preparing a third solution by dissolving zinc salt and iron(III) salt in purified water; e) adding the third solution dropwise into the solution resulting from step c); f) drying the solution resulting from step e) to form a dried mixed metal EDTA complex; and g) calcining said dried mixed metal EDTA complex in air to obtain said $ZnFe_2O_4$ catalyst.

DETAILED DESCRIPTION OF THE INVENTION

Figure 1:
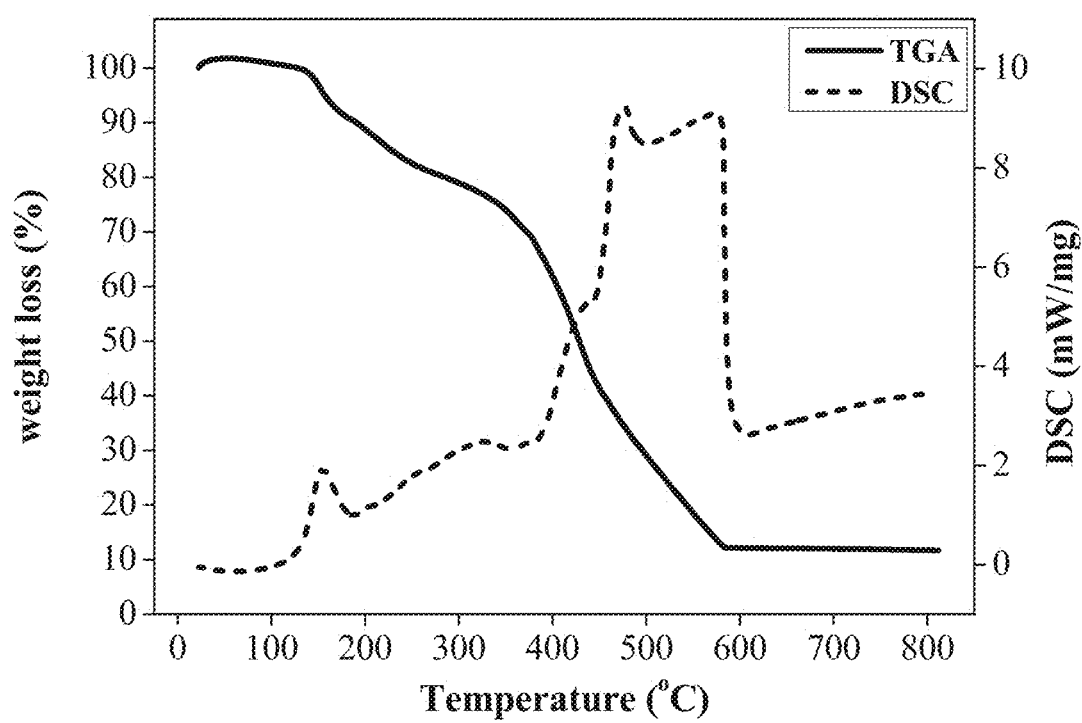
FIG. 1 shows the results of differential scanning calorimetry (DSC) and thermogravimetric analysis (TGA) of the bimetallic Zn—Fe containing EDTA complex used in one embodiment of this invention.

This present invention generally discusses a new class of bimetallic zinc-iron catalyst system ($ZnFe_2O_4$) that can be synthesized by low temperature controlled decomposition of Zn—Fe containing EDTA complex with PVP as surfactant. The $ZnFe_2O_4$ catalyst may simultaneously catalyze the esterification of FFAs and transesterification of triglycerides present in low grade feedstocks. This catalyst system exhibits a higher degree of tolerance towards FFAs and can be easily recycled and reused for over twenty cycles of the one-step simultaneous reaction.

Ethylenediaminetetraacetic acid (EDTA) is a multi-dentate ligand that used as chelating agent to coordinate the Zn(II) and Fe(III) ions to form a bimetallic complex. The bimetallic complex assures that two metal ions are well-mixed so that the chance for making well mixed bimetallic oxide is increased. PVP is a neutral polymer acted as a surfactant to form micelles that control the size of the nanoparticles and prevent from aggregation of nanomaterials. In addition, the decomposition temperature is significantly decreased as the metal precursor is a tailor designed organometallic complex instead of inorganic metal salt.

In one embodiment, this invention provides a catalyst for catalyzing the esterification of fatty acids or transesterification of triglycerides, comprising $ZnFe_2O_4$ spinel nanoparticles. In another embodiment, said $ZnFe_2O_4$ has lattice parameters of a=b=c=8.42 Å. In a further embodiment, said $ZnFe_2O_4$ has a surface basic strength of between 6.8 and 7.2. In one embodiment, said $ZnFe_2O_4$ has a binding energy of 1022.0 eV for Zn $2p_{3/2}$, 711.5 eV for Fe $2p_{3/2}$, 725.1 eV for Fe $2p_{1/2}$, 530.6 eV for O 1s of lattice oxygen, and 531.9 eV for O 1s of hydroxyl oxygen. In another embodiment, said $ZnFe_2O_4$ has a lattice oxygen to hydroxyl oxygen ratio of at least 2. In a further embodiment, said ratio of lattice oxygen to hydroxyl oxygen is 3.83. In one embodiment, said $ZnFe_2O_4$ has a particle size between 30 and 60 nm. In another embodiment, said $ZnFe_2O_4$ has a Zn:Fe surface atomic ratio of 0.4 or up to 0.6.

In one embodiment, said $ZnFe_2O_4$ has a surface area ranging from 20 $m^2/g$ to 100 $m^2/g$. In a preferred embodiment, said $ZnFe_2O_4$ has a surface area of about 39.2 $m^2/g$. In another embodiment, said $ZnFe_2O_4$ has a pore volume ranging from 0.1 ml/g to 0.6 ml/g. In a preferred embodiment, said $ZnFe_2O_4$ has a pore volume of about 0.24 ml/g. In a further embodiment, said $ZnFe_2O_4$ has an average pore size ranging from 1 nm to 15 nm. In a preferred embodiment, said $ZnFe_2O_4$ has an average pore size of about 2 nm.

In one embodiment, this invention provides a method for transesterification, comprising the steps of: providing a catalyst comprising $ZnFe_2O_4$; contacting said catalyst with one or more alcohols and a composition comprising one or more esters to form a reaction mixture; and heating said reaction mixture to form transesterification products.

In one embodiment, said one or more esters are triglycerides, wherein the fatty acid portions of said triglycerides are selected from the group consisting of acetic acid, propanoic acid, butanoic acid, pentanoic acid, hexanoic acid, heptanoic acid, octanoic acid, nonanoic acid, capric acid, undecanoic acid, lauric acid, tridecanoic acid, myristic acid, myristoleic acid, pentadecanoic acid, palmitic acid, palmitoleic acid, sapienic acid, heptadecanoic acid, stearic acid, oleic acid, elaidic acid, vaccenic acid, petroselinic acid, linoleic acid, linolelaidic acid, linolenic acid, stearidonic acid, nonadecanoic acid, eicosanoic acid, gadoleic acid, gondoic acid, paullinic acid, dihomo-γ-linolenic acid, mead acid, arachidonic acid, eicosapentaenoic acid, heneicosanoic acid, behenic acid, erucic acid, adrenic acid, docosahexaenoic acid, tricosanoic acid, lignoceric acid, nervonic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, ceroplastic acid, hexatriacontanoic acid, heptatriacontanoic acid and octatriacontanoic acid. In certain embodiments, said one or more alcohols are selected from the group consisting of methanol, ethanol, propanol, butanol, pentanol, hexanol, heptanol, octanol, nonanol, decanol and the isomers thereof. In one embodiment, said composition comprising one or more esters is a biodiesel feedstock.

In another embodiment, said composition further comprises one or more free fatty acids selected from the group consisting of acetic acid, propanoic acid, butanoic acid, pentanoic acid, hexanoic acid, heptanoic acid, octanoic acid, nonanoic acid, capric acid, undecanoic acid, lauric acid, tridecanoic acid, myristic acid, myristoleic acid, pentadecanoic acid, palmitic acid, palmitoleic acid, sapienic acid, heptadecanoic acid, stearic acid, oleic acid, elaidic acid, vaccenic acid, petroselinic acid, linoleic acid, linolelaidic acid, linolenic acid, stearidonic acid, nonadecanoic acid, eicosanoic acid, gadoleic acid, gondoic acid, paullinic acid, dihomo-γ-linolenic acid, mead acid, arachidonic acid, eicosapentaenoic acid, heneicosanoic acid, behenic acid, erucic acid, adrenic acid, docosahexaenoic acid, tricosanoic acid, lignoceric acid, nervonic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, ceroplastic acid, hexatriacontanoic acid, heptatriacontanoic acid and octatriacontanoic acid for enhancing the reaction rate and conversion of said one or more esters. In another embodiment, said one or more free fatty acids make up 0.5 wt % to 50.0 wt % of the reactants. In yet another embodiment, said catalyst simultaneously catalyzes esterification of said one or more fatty acids. In a further embodiment, the number of moles of said one or more alcohols is at least six times the total number of moles of both said one or more esters and said one or more fatty acids. In one embodiment, said reaction mixture is heated at a temperature range from 100° C. to 300° C. In another embodiment, the reaction mixture is heated for 2 hours to 24 hours. In another embodiment, said reaction mixture comprises 2 wt % to 8 wt % of $ZnFe_2O_4$.

In one embodiment, this invention provides a method for transesterification of triglycerides, comprising the steps of: providing a catalyst comprising $ZnFe_2O_4$; contacting said catalyst with an alcohol and a composition comprising triglycerides to form a reaction mixture; heating said reaction mixture to form transesterification products of the triglycerides. In one embodiment, said composition comprising triglycerides is a biodiesel feedstock. In another embodiment, said composition further comprises free fatty acids for enhancing reaction rate and conversion of said triglycerides. In a further embodiment, said free fatty acids make up at least 0.5 wt. % of said reaction mixture. In another embodiment, said free fatty acids make up 4.5 wt. % of said reaction mixture. In yet another embodiment, said catalyst simultaneously catalyzes the esterification of said fatty acids to the corresponding esterification products. In one embodiment, said reaction mixture has at least six times more molecules of alcohol than the sum of triglycerides and fatty acids. In another embodiment, said reaction mixture has at least twenty times more molecules of alcohol than the sum of triglycerides and fatty acids. In a further embodiment, said alcohol is one or more selected from the group consisting of methanol, ethanol, propanol, butanol, pentanol, hexanol and heptanol. In one embodiment, said reaction mixture is heated at a temperature of at least 100° C. In another embodiment, said reaction mixture is heated at a temperature of 140° C. or above. In one embodiment, the reaction mixture is heated for at least 2 hours. In another embodiment, the reaction mixture is heated for 9 hours. In yet another embodiment, the reaction mixture is heated for 4 hours in the presence of free fatty acids. In one embodiment, said reaction mixture comprises at least 2 wt. % of $ZnFe_2O_4$. In another embodiment, said reaction mixture comprises 8 wt. % of $ZnFe_2O_4$.

In one embodiment, this invention further provides a method for preparing a $ZnFe_2O_4$ catalyst, comprising the steps of: a) preparing a first solution by dissolving ethylenediaminetetraacetic acid (EDTA) in purified water, followed by adding a base until the pH is 3 to 10; b) preparing a second solution by dissolving a surfactant in purified water; c) adding the second solution dropwise to the first solution; d) preparing a third solution by dissolving zinc salt and iron(III) salt in purified water; e) adding the third solution dropwise into the solution resulting from step c); f) drying the solution resulting from step (e) to form a dried mixed metal EDTA complex; and g) calcining said dried mixed metal EDTA complex in air to obtain said $ZnFe_2O_4$ catalyst. In an embodiment, said base is selected from the group consisting of ammonia water ($NH_4OH$), potassium hydroxide (KOH) and sodium hydroxide (NaOH). In a preferred embodiment, said base is ammonia water ($NH_4OH$). In another embodiment, said surfactant is selected from the group consisting of polyvinylpyrrolidone (PVP), polyvinyl alcohol (PVA), poly(acrylic acid) (PAA), poly(malic acid), poly(acrylic acid-co-malic acid), poly(ethyleneimine) (PEI), ethylene glycol (EG), polyethylene glycol (PEG) and polyethylene glycol tert-octylphenyl ether. In a preferred embodiment, said surfactant is polyvinylpyrrolidone. In an embodiment, said surfactant has an average molecular weight of 400 to 55000. In a preferred embodiment, said surfactant has an average molecular weight of 40000. In another embodiment, said zinc salt is selected from the group consisting of zinc nitrate hexahydrate ($Zn(NO_3)_2.6H_2O$), zinc chloride ($ZnCl_2$), zinc sulphate heptahydrate ($ZnSO_4.7H_2O$), zinc oxalate ($ZnC_2O_4$), zinc acetate dihydrate ($Zn(CH_3COO)_2.2H_2O$), zinc citrate dihydrate ($(C_6H_5O_7)_2Zn_3.2H_2O$), zinc oxide (ZnO), zinc hydroxide ($Zn(OH)_2$), zinc carbonate ($ZnCO_3$) and zinc carbonate basic ($[ZnCO_3]_2.[Zn(OH)_2]_3$). In a preferred embodiment, said zinc salt is zinc nitrate hexahydrate ($Zn(NO_3)_2.6H_2O$). In one embodiment, said iron (III) salt is selected from the group consisting of iron (II) nitrate ($Fe(NO_3)_2$), iron (III) nitrate nonahydrate ($Fe(NO_3)_3.9H_2O$), iron (II) chloride tetrahydrate ($FeCl_2.4H_2O$), iron (III) chloride hexahydrate ($FeCl_3.6H_2O$), iron (II) sulphate heptahydrate ($FeSO_4.7H_2O$), iron (III) sulphate ($Fe_2(SO_4)_3$), iron (II) oxalate dihydrate ($FeC_2O_4.2H_2O$), iron (III) oxalate hexahydrate ($Fe_2(C_2O_4)_3.6H_2O$), iron (II) acetate ($Fe(CH_3COO)_2$), iron (III) citrate ($C_6H_5O_7Fe$), iron (II) oxide (FeO), iron (III) oxide ($Fe_2O_3$), iron (II) hydroxide ($Fe(OH)_2$), iron (III) hydroxide ($Fe(OH)_3$), iron (II) carbonate ($FeCO_3$), iron (III) carbonate ($Fe_2(CO_3)_3$) and iron oxide hydroxide (FeOOH). In a preferred embodiment, said iron (III) salt is iron (III) nitrate nonahydrate ($Fe(NO_3)_3.9H_2O$). In one embodiment, said dried mixed metal EDTA complex is obtained by drying at a temperature ranging from 60° C. to 110° C. In another embodiment, said mixed metal EDTA complex is calcined for 1 hour to 6 hours. In another embodiment, said mixed metal EDTA complex is calcined for 5 hours. In another embodiment, said mixed metal EDTA complex is calcined at a temperature ranging from 300° C. to 700° C. In one embodiment, said mixed metal EDTA complex is calcined at 600° C. in air.

The invention will be better understood by reference to the Experimental Details which follow, but those skilled in the art will readily appreciate that the specific experiments are provided only for illustrative purpose, and are not meant to limit the invention scope as described herein, which is defined by the claims following thereafter.

Throughout this disclosure, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended, and does not exclude additional, un-recited elements or method steps.

Example 1

Preparation of Catalyst

The $ZnFe_2O_4$ catalyst was prepared by the following steps: (a) a first solution was prepared by dissolving ethylenediaminetetraacetic acid (10 g) in milli-Q water (200 mL), followed by adding four equivalents of ammonia water (10.5 mL) until the pH equals to 6; (b) a second solution was prepared by dissolving polyvinylpyrrolidone with molecular weight of 40000 (18.924 g) in milli-Q water (400 mL); (c) the second solution was added dropwise to the first solution and was allowed to stir vigorously at 60° C. for 15 minutes; (d) a third solution was obtained by dissolving zinc nitrate hexahydrate (5.092 g) and iron (III) nitrate nonahydrate (13.832 g) in milli-Q water (200 ml); (e) the third solution was added dropwise into the solution from step (c) and then the mixture was stirred for 30 minutes; (f) after stirring, the solution was dried at 110° C. overnight; (g) the dried mixed metal EDTA complex was calcined in air at 600° C. for 5 hours.

Example 2

Material Characterization (1) Differential Scanning Calorimetry (DSC) and Thermogravimetric Analysis (TGA)

The bimetallic Zn—Fe containing EDTA complex was subjected to differential scanning calorimetry (DSC) and thermogravimetric analysis (TGA) as illustrated in FIG. 1 in order to find out the optimal decomposition temperature. The DSC/TGA recorded the weight loss and the phase changes of bimetallic complex from 30° C. to 800° C. under a stream of flowing air. The DSC curve displayed a slightly endothermic transformation followed by an exothermic peak with a total weight loss of 8% observed in TGA from 30° C. to 160° C., mainly due to the removal of moisture. With the temperature at 320° C., an exothermic transformation in DSC and a 20% weight loss observed in TGA were attributed to the decomposition of EDTA organic-based ligand. A broad exothermic band with two shoulder peaks is observed at 470° C. and 570° C. in DSC with a total weight loss of 62%, likely due to the decomposition of PVP and the recrystallization of $ZnFe_2O_4$ in spinel structure. The transformation of bimetallic complex to $ZnFe_2O_4$ was complete at 600° C. as no further phase changes and weight loss were found in DSC and TGA respectively above 600° C., and thus the optimal decomposition temperature for synthesis of spinel $ZnFe_2O_4$ was determined to be 600° C.

(2) Scanning Electron Microscopy (SEM) and Transmission Electron Microscopy (TEM)

Figure 2A:
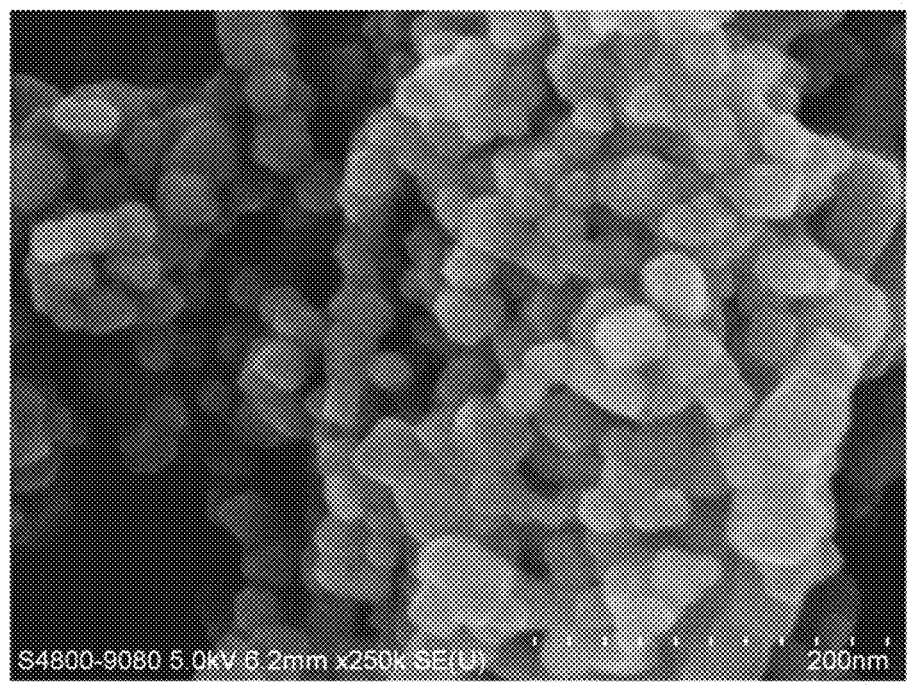
FIG. 2A shows the SEM micrograph of the $ZnFe_2O_4$ catalyst in the form of a nanoparticle with a particle size of 34.5±4.2 nm.
Figure 2B:
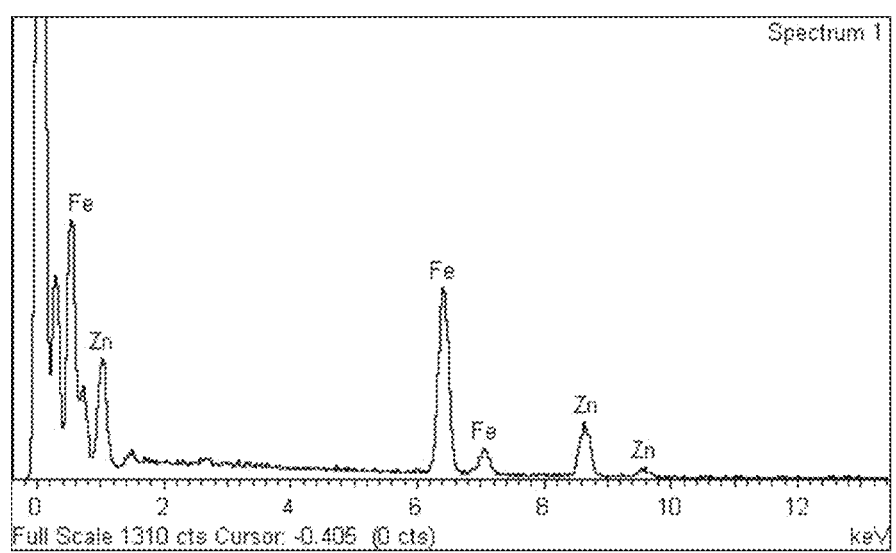
FIG. 2B shows the Energy dispersive X-ray (EDX) spectroscopy results of the $ZnFe_2O_4$ catalyst.
Figure 3A:
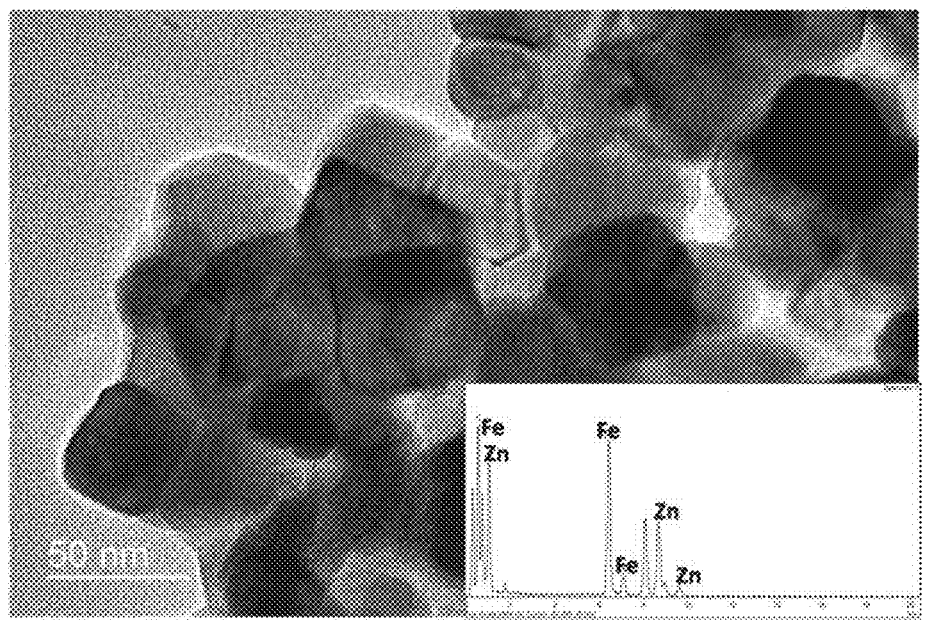
FIG. 3A shows the TEM micrograph of the $ZnFe_2O_4$ catalyst having an average particle size of 48.2±5.9 nm.
Figure 3B:
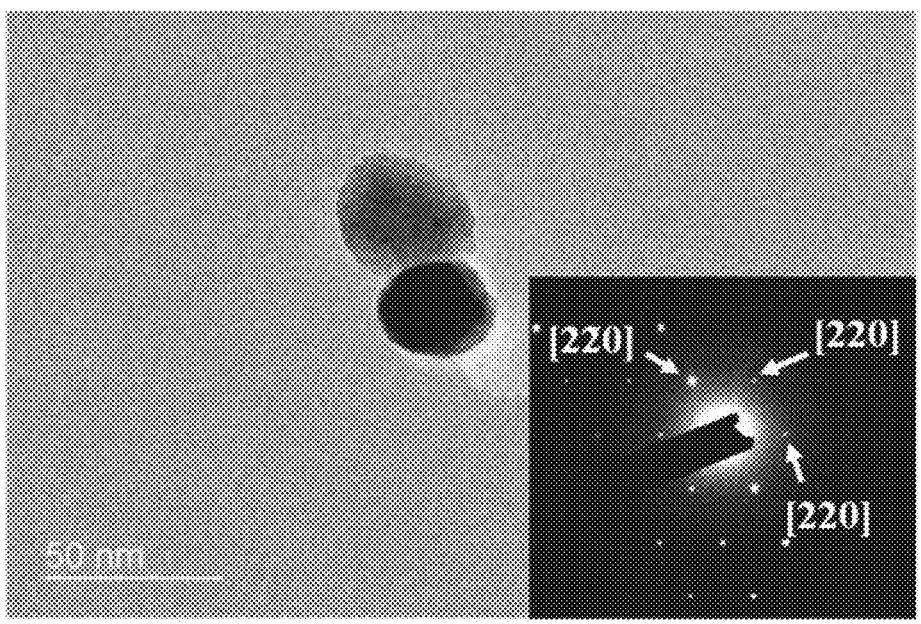
FIG. 3B shows the HR-TEM of an individual nanoparticle having a single crystalline form.

The $ZnFe_2O_4$ catalyst synthesized according to example 1 was characterized by scanning electron microscopy (SEM) and transmission electron microscopy (TEM). The SEM micrograph as depicted in FIG. 2A shows the $ZnFe_2O_4$ catalyst to be nanoparticles with a particle size of 34.5±4.2 nm. TEM analysis shown in FIG. 3A verifies that the average particle size of the nanoparticles is 48.2±5.9 nm. As illustrated in FIG. 3B, the HR-TEM of an individual nanoparticle reveals a single crystalline form. The crystal plane with d-spacing of 0.29 nm is attributed to [220] crystal plane of $ZnFe_2O_4$ in spinel structure. The elemental composition of $ZnFe_2O_4$ conducted by energy dispersive X-ray spectroscopy (EDX) in SEM and TEM as tabulated in TABLE 1 suggests that the atomic ratio of zinc-to-iron is 0.55.

TABLE 1

|  | Atomic percentage in SEM (%) | | | Atomic percentage in TEM (%) | | |
| --- | --- | --- | --- | --- | --- | --- |
|  | Zn | Fe | Zn/Fe | Zn | Fe | Zn/Fe |
| DC-ZnFe$_2$O$_4$ | 35.4 | 64.6 | 0.55 | 35.6 | 64.4 | 0.55 |

(3) X-Ray Diffraction (XRD)

Figure 4:
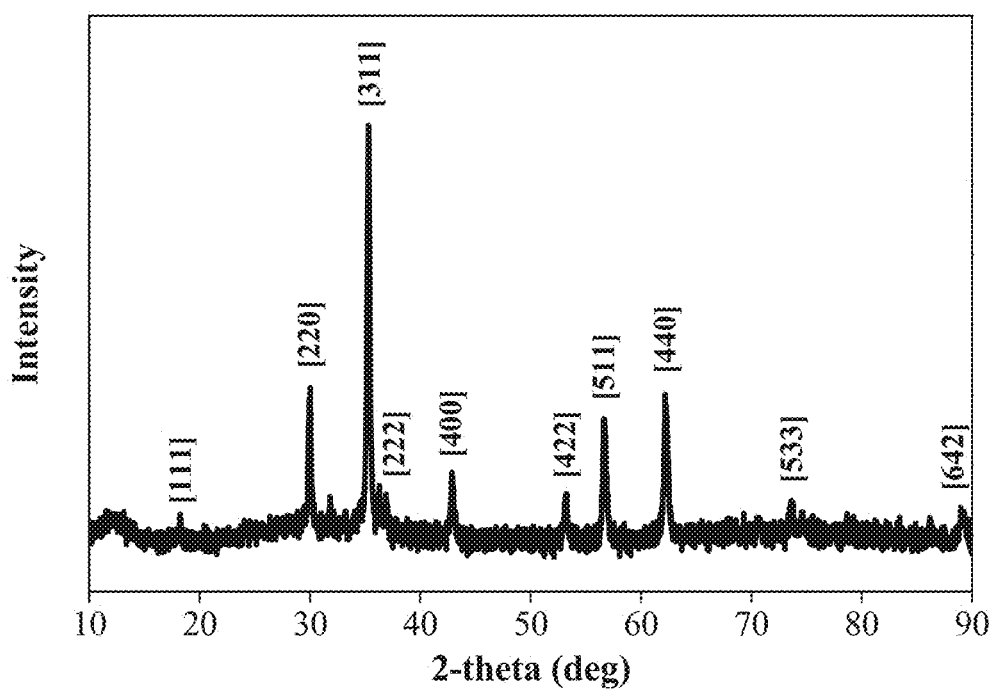
FIG. 4 shows the powder X-ray diffraction (XRD) results of the $ZnFe_2O_4$ catalyst.

The crystal structure of the $ZnFe_2O_4$ catalyst was analyzed by powder X-ray diffraction (XRD) with the result illustrated in FIG. 4. The XRD pattern demonstrates a high degree of crystallinity and well-matched with the standard pattern of cubic crystal structure of spinel phased zinc ferrite with space group of Fd-3m (ICDD card No.: 01-074-8584). No diffraction peaks from other crystalline forms were detected, demonstrating that the $ZnFe_2O_4$ catalyst is free from zinc oxide (ZnO) and iron oxide ($Fe_2O_3$). As tabulated in TABLE 2, the average grain size and the crystalline size of the $ZnFe_2O_4$ catalyst were found to be 25.9 nm and 27.5 nm respectively, exhibiting the lattice parameter of a=b=c=8.42 Å.

TABLE 2

|  | Average grain size (nm) | Crystalline size (nm) | Lattice constant | | |
| --- | --- | --- | --- | --- | --- |
|  |  |  | a (Å) | b (Å) | c (Å) |
| ZnFe$_2$O$_4$ | 25.9 | 27.5 | 8.42 | 8.42 | 8.42 |

(4) Fourier Transform Infra-Red Spectroscopy (FTIR)

Figure 5:
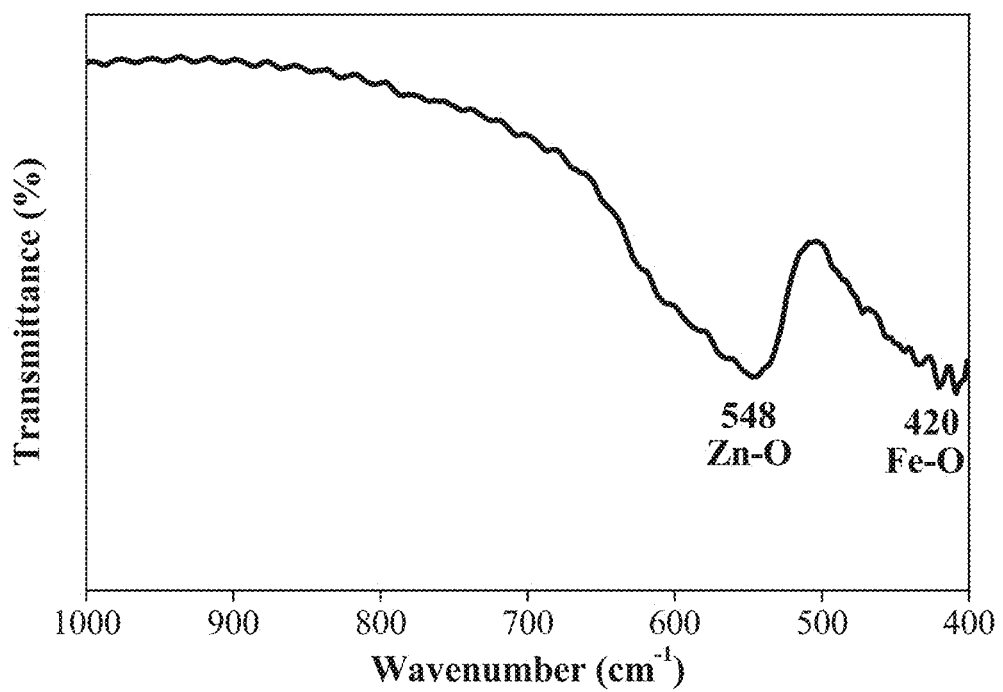
FIG. 5 shows the FTIR spectrum of the $ZnFe_2O_4$ catalyst with absorption bands at 420.64 $cm^{-1}$ and 406.90 $cm^{-1}$ in the fingerprint region ascribed to the intrinsic stretching of Fe—O in octahedral positions and an absorption band at 547.63 $cm^{-1}$ attributed to the intrinsic stretching of Zn—O in tetrahedral positions.

The tetrahedral (A-site) and octahedral (B-site) positions in normal spinel $ZnFe_2O_4$ are normally occupied by Zn(II) and Fe(III) ions respectively, in which the tetrahedral and octahedral positions were investigated by Fourier transform infra-red spectroscopy (FTIR). The FTIR spectrum of the $ZnFe_2O_4$ catalyst as depicted in FIG. 5 shows that the absorption bands at 420.64 cm$^{-1}$ and 406.90 cm$^{-1}$ in fingerprint region is ascribed to the intrinsic stretching of Fe—O in octahedral positions while an absorption band at 547.63 cm$^{-1}$ is attributed to the intrinsic stretching of Zn—O in tetrahedral positions.

(5) X-Ray Photoelectron Spectroscopy (XPS)

Figure 6A:
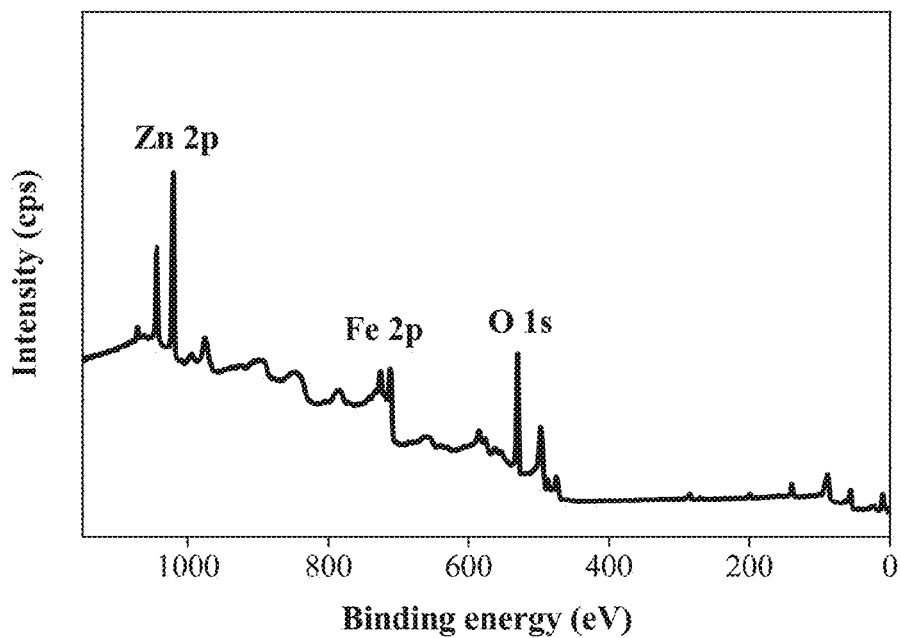
FIG. 6A shows an X-ray photoelectron spectrum of the $ZnFe_2O_4$ catalyst for determining the oxidation state of each element and surface composition.
Figure 6B:
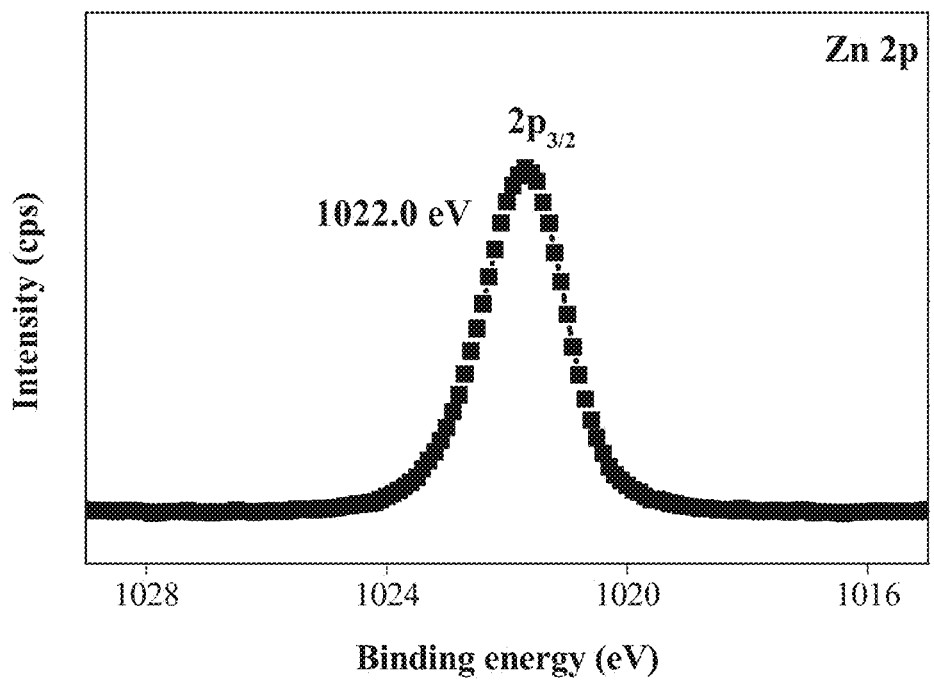
FIG. 6B shows the Zn $2p_{3/2}$ transition of $ZnFe_2O_4$.
Figure 6C:
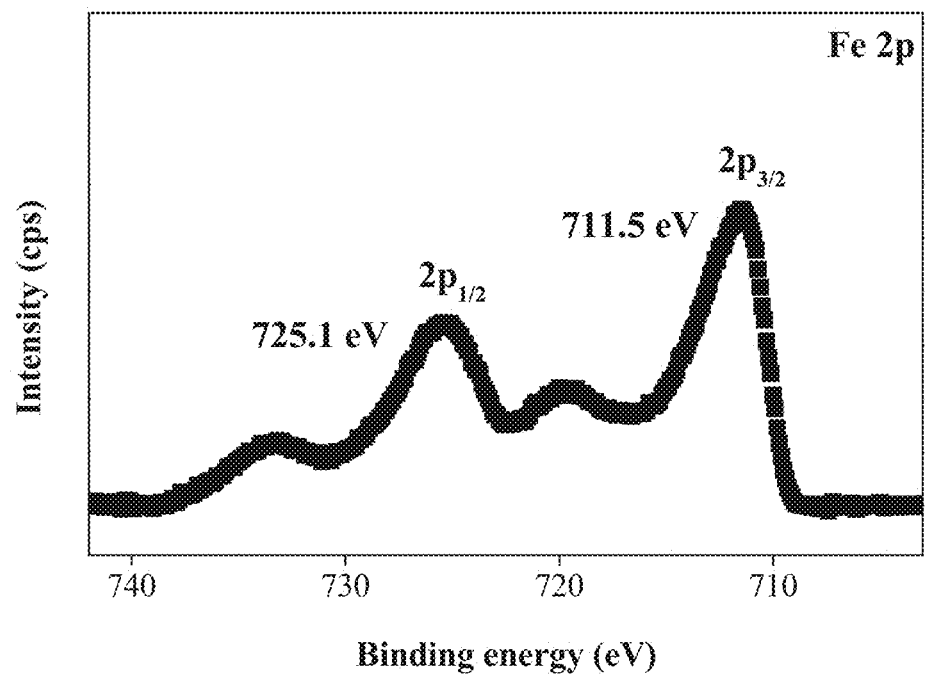
FIG. 6C shows the Fe $2p_{3/2}$ and Fe $2p_{1/2}$ transitions of $ZnFe_2O_4$.
Figure 6D:
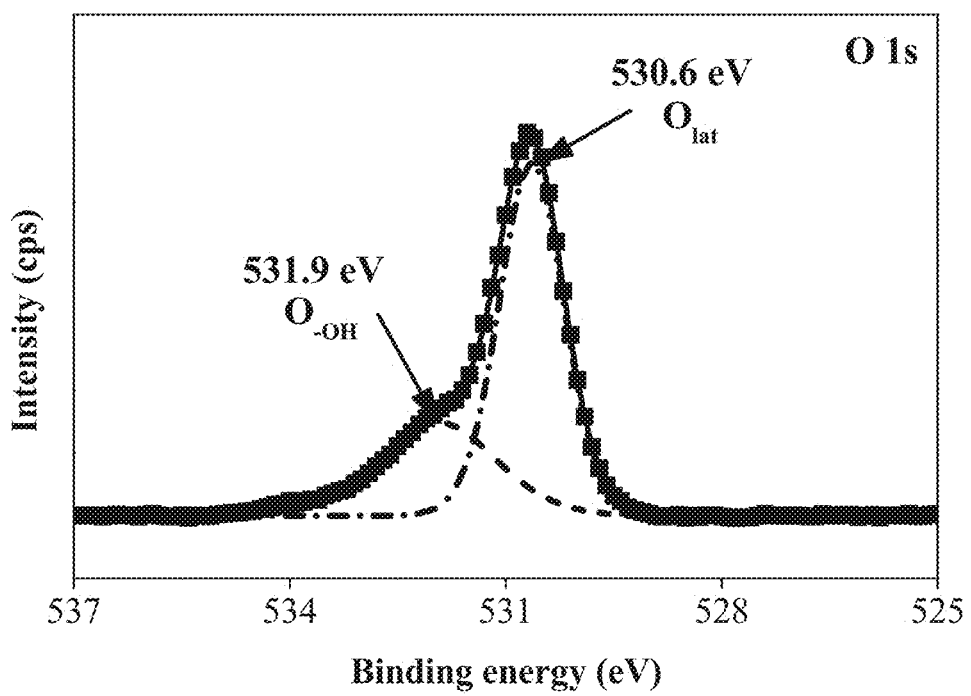
FIG. 6D shows the lattice oxygen ($O_{lat}$) and surface hydroxyl oxygen ($O_{-OH}$) transitions of $ZnFe_2O_4$.

The core level spectra of Zn 2p, Fe 2p and O 1s was collected by X-ray photoelectron spectroscopy (XPS) as illustrated in FIG. 6A in order to determine the oxidation state of each element and the surface composition of the $ZnFe_2O_4$ catalyst. The peak at 1022.0 eV is attributed to Zn $2p_{3/2}$ which verifies the presence of Zn(II) ion in the $ZnFe_2O_4$ catalyst (FIG. 6B). The element of iron is found in 3+ state with two peaks observed at 711.5 eV and 725.1 eV which are assigned to the Fe $2p_{3/2}$ and Fe $2p_{1/2}$ respectively (FIG. 6C). The asymmetric peak located at 530.7 eV is corresponded to the O 1s region (FIG. 6D). It was further resolved into two distinguishable sub-peaks at 530.6 eV and 531.9 eV which are ascribed to the lattice oxygen ($O_{lat}$) and surface hydroxyl oxygen ($O_{-OH}$) respectively. By comparing the intensities of each element, the surface atomic ratios of zinc, iron and oxygen were normalized and tabulated in TABLE 3. The surface atomic ratio of Zn-to-Fe on the catalyst surface is found to be 0.49 while the ratio of $O_{lat}$-to-$O_{-OH}$ is found to be 3.83.

TABLE 3

| | Atomic ratio (%) | | | | | |
| --- | --- | --- | --- | --- | --- | --- |
| | Zn | Fe | Zn/Fe | $O_{lat}$ | $O_{-OH}$ | $O_{lat}/O_{-OH}$ |
| DC-ZnFe$_2$O$_4$ | 15.69 | 32.20 | 0.49 | 41.31 | 10.80 | 3.83 |

(6) Determination of Surface Basic Strength by Hammett Indicator Analysis

It is important to investigate the correlation between the catalytic performance and the surface basic strength of the $ZnFe_2O_4$ catalyst as the basic sites on the catalyst surface are known to be the active sites for the simultaneous reaction. The surface basic strength (H_) of the $ZnFe_2O_4$ was found to be in the range of 6.8<H_<7.2 by Hammett indicator analysis. It demonstrates the amphoteric property on the catalyst surface and speculates the $ZnFe_2O_4$ to be a heterogeneous catalyst in the one-step simultaneous esterification and transesterification reaction.

(7) Determination of Surface Area, Pore Volume and Average Pore Size

Figure 12A:
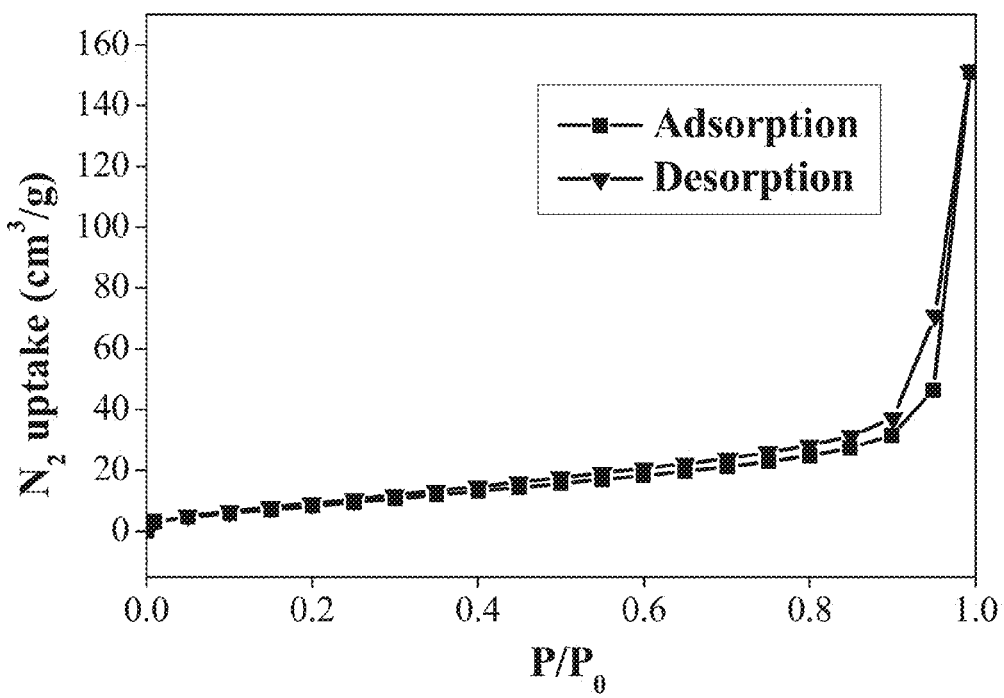
FIG. 12A shows the $N_2$ adsorption-desorption isotherms for the determination of surface area of the $ZnFe_2O_4$ catalyst.
Figure 12B:
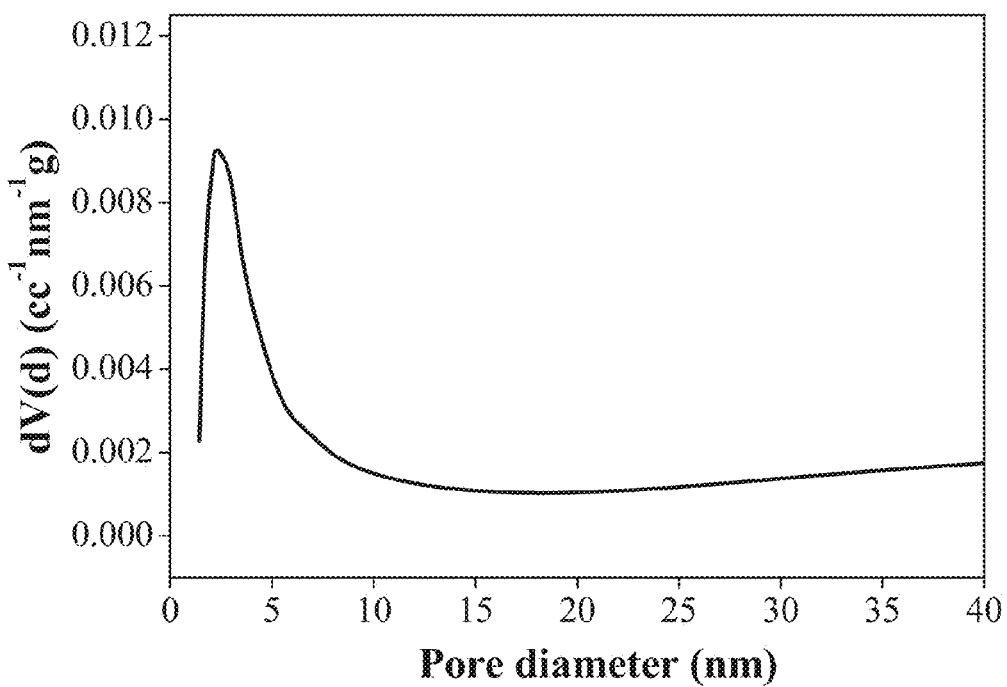
FIG. 12B shows the pore size distribution of the $ZnFe_2O_4$ catalyst.

The surface area and porosity analysis were performed using a Quantachrome Autosorb iQ gas sorption analyzer. The $ZnFe_2O_4$ sample was outgassed at 0.03 Tarr with a 2° C. min$^{-1}$ ramp to 130° C. and held at 130° C. for 20 hours. The analysis was performed under vacuum. Nitrogen adsorption-desorption isotherm at 283 K was performed on a Quantachrome Autosorb 1 MP instrument. Pore analysis was performed using $N_2$ at 77 K (P/P$_0$ range 1×10$^{-5}$ to 0.995) (FIG. 12A). In this manner, the surface area of the bimetallic $ZnFe_2O_4$ catalyst was found to be 39.2 m$^2$/g. Furthermore, the pore volume on the catalyst surface was found to be 0.24 cm$^3$/g, and the pore diameter was determined to be 2 nm, an indication that the catalyst was a mesoporous material (FIG. 12B).

Example 3

Catalytic Activities of ZnFe$_2$O$_4$ Catalyst

Various low grade feedstock as listed in TABLE 4 may serve as a replacement to the refined vegetable oil for the biodiesel production in order to reduce the production cost; however, a higher degree of FFA is found in the feedstock. The FFA content and the acid value generally ranged from 0.11 wt. % to 4.93 wt. % and from 0.22 mg$_{KOH}$/g to 9.78 mg$_{KOH}$/g, respectively. Among all feedstock, refined food grade canola oil gives the lowest acid value while the crude *Jatropha* oil gives the highest acid value. The evaluation of ZnFe$_2$O$_4$ catalyzed transesterification suggests that the catalyst performs well with over 90% conversion no matter how much FFA exists in the low grade feedstock. It is surprising to find out that the ZnFe$_2$O$_4$ catalyst tolerates a high degree of FFA and can successfully be applied to biodiesel production from low grade feedstock.

TABLE 4

| Feedstock | FFA content (wt. %) | Acid value (mg$_{KOH}$/g) | Water content (wt. %) | Conversion[a] (%) |
|---|---|---|---|---|
| Refined food grade canola oil | 0.11 | 0.22 | 0.13 | 98.7 |
| Refined rice bran oil | 0.43 | 0.87 | 0.15 | 92.3 |
| Crude peanut oil | 0.45 | 0.90 | 0.11 | 97.3 |
| Crude sesame oil | 0.46 | 0.91 | 0.11 | 98.4 |
| Waste cooking oil | 0.65 | 1.29 | 0.12 | 97.5 |
| Crude flaxseed oil | 1.16 | 2.32 | 0.12 | 96.8 |
| Crude canola oil | 1.65 | 3.28 | 0.13 | 97.7 |
| Crude rice bran oil | 2.00 | 3.98 | 0.11 | 96.7 |
| Crude *Camelina* oil | 3.86 | 7.65 | 0.04 | 99.7 |
| Crude *Jatropha* oil | 4.93 | 9.78 | 0.13 | 99.6 |

[a]Reaction conditions: feedstock-to-methanol molar ratio (1:20), catalyst loading (6 wt. %), reaction temperature (140° C.) and reaction time (9 h).

Since the availability of FFA in feedstock may affect the catalytic rate of reaction, Taguchi analysis, which consists of orthogonal array experimental design (OA), signal-to-noise (S/N) ratio analysis and range analysis, was employed to optimize the catalytic conditions for the one-step simultaneous reaction. Three main factors including feedstock-to-methanol molar ratio (factor A), catalyst loading (factor B) and oleic acid loading (factor C) were used, each at four different values, as shown in TABLE 5.

TABLE 5

| | Factor | | |
|---|---|---|---|
| Level | Feedstock:MeOH molar ratio A | Catalyst loading B (wt. %) | Oleic acid loading C (wt. %) |
| 1 | 1:10 | 2 | 2.00 |
| 2 | 1:20 | 4 | 18.00 |
| 3 | 1:30 | 6 | 34.00 |
| 4 | 1:40 | 8 | 50.00 |

Figure 7:
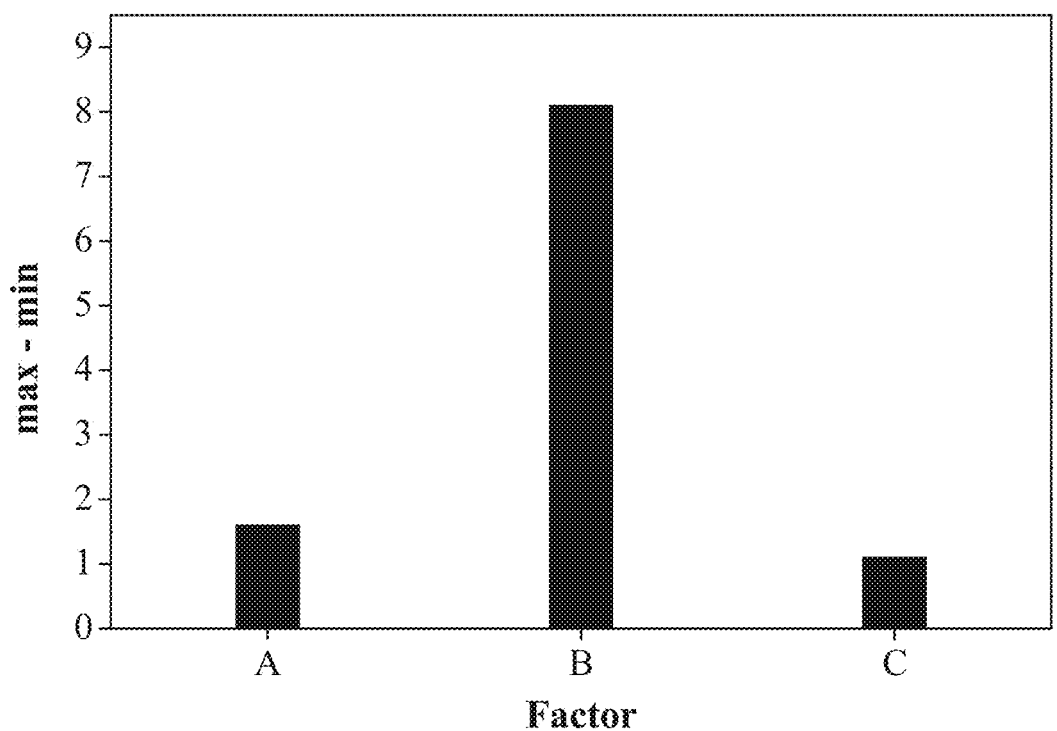
FIG. 7 shows the result of a range analysis for three factors in the catalytic reaction wherein factor A is the ratio of feedstock:MeOH, B is the catalyst loading, and C is the oleic acid loading.

Referring to the OA$_{16}$ experimental design, sixteen different experimental trials and the completed optimization process were designed and carried out at a fixed temperature of 140° C. for a fixed reaction time of 2 h. The remaining column is ascribed to the experimental errors which show the reliability of the entire optimization process. As tabulated in TABLE 6, the result shows the average conversion (Y$_i$), where i=1-16, for each experimental trial. The conversion and the corresponding S/N ratios ranged from 27.4% to 75.5% and 28.73 to 37.55 respectively. These data are taken as the original data and employed for the calculation of mean signal-to-noise ratio ($\overline{S_{ji}}$) values. The highest $\overline{S_{ji}}$ value of each factor was assigned as the optimal reaction condition for the one-step simultaneous reaction. The highest $\overline{S_{ji}}$ value for each factor as shown in TABLE 7 is defined in a combination of A$_2$B$_4$C$_1$, wherein the feedstock-to-methanol molar ratio is 1:20 (34.7), catalyst loading is 8 wt. % (36.9) and the oleic acid loading is 2 wt. % (34.7). As depicted in FIG. 7, the significance for each factor is displayed in an ascending order of oleic acid loading (1.1)<feedstock-to-methanol molar ratio (1.6)<catalyst loading (8.1). It is observed that the catalyst loading (factor B) exhibits the largest range value which indicates the most significant factor to the catalytic conversion.

According to the TABLE 7 TABLE 7, a decreasing trend of the $\overline{S_{Ai}}$ values with an increase of feedstock-to-methanol ratio from 1:20 to 1:40 indicates a decrease of the feedstock conversion. Increasing the optimal ratio (1:20) does not increase the yield of the reaction as larger amounts of methanol lower the substrate concentration in the reaction mixture. It is observed that an increasing trend of $\overline{S_{Bi}}$ values indicates that feedstock conversion increase with an increase of catalyst loading from 2 wt. % to 8 wt. %. With an increase in the catalyst loading, more active sites (Lewis basic sites) are available for alkoxide generation to facilitate the simultaneous reaction, thus increasing the yield of the reaction. For the $\overline{S_{Ci}}$ value, it is found that conversion increases with increasing oleic acid loading from 2.00 wt. % to 34.00 wt. %. When more water molecules were generated during the simultaneous reaction, the equilibrium position could be shifted backward, and therefore the biodiesel yield would decrease.

TABLE 6

| | Factor | | | Conversion (%) | | | Average | | S/N |
|---|---|---|---|---|---|---|---|---|---|
| Entry | Feedstock:MeOH molar ratio A | Catalyst loading B | Oleic acid loading C | y$_1$ | y$_2$ | y$_3$ | Y (%) | SD | ratio |
| 1 | 1:10 | 2 | 2.00 | 28.4 | 27.5 | 27.2 | 27.7 | 0.6 | 28.85 |
| 2 | 1:10 | 4 | 18.00 | 68.8 | 69.8 | 69.9 | 69.5 | 0.6 | 36.84 |
| 3 | 1:10 | 6 | 34.00 | 66.1 | 65.6 | 65.7 | 65.8 | 0.3 | 36.36 |
| 4 | 1:10 | 8 | 50.00 | 65.8 | 65.9 | 64.4 | 65.4 | 0.8 | 36.31 |
| 5 | 1:20 | 2 | 18.00 | 27.4 | 27.6 | 28.2 | 27.7 | 0.4 | 28.86 |
| 6 | 1:20 | 4 | 2.00 | 73.2 | 73.3 | 70.8 | 72.4 | 1.4 | 37.20 |
| 7 | 1:20 | 6 | 50.00 | 57.0 | 57.4 | 57.4 | 57.3 | 0.2 | 35.16 |
| 8 | 1:20 | 8 | 34.00 | 74.8 | 76.9 | 74.7 | 75.5 | 1.2 | 37.55 |
| 9 | 1:30 | 2 | 34.00 | 29.5 | 26.3 | 26.5 | 27.4 | 1.8 | 28.73 |
| 10 | 1:30 | 4 | 50.00 | 53.5 | 50.4 | 50.8 | 51.6 | 1.7 | 34.24 |
| 11 | 1:30 | 6 | 2.00 | 62.8 | 64.5 | 63.2 | 63.5 | 0.9 | 36.05 |

TABLE 6-continued

| | Factor | | | | | | | |
|---|---|---|---|---|---|---|---|---|
| | Feedstock:MeOH | Catalyst | Oleic acid | Conversion (%) | | | Average | | S/N |
| Entry | molar ratio A | loading B | loading C | $y_1$ | $y_2$ | $y_3$ | Y (%) | SD | ratio |
| 12 | 1:30 | 8 | 18.00 | 70.7 | 69.7 | 71.3 | 70.6 | 0.8 | 36.97 |
| 13 | 1:40 | 2 | 50.00 | 27.4 | 27.3 | 28.4 | 27.7 | 0.6 | 28.85 |
| 14 | 1:40 | 4 | 34.00 | 40.1 | 39.0 | 39.7 | 39.6 | 0.6 | 31.95 |
| 15 | 1:40 | 6 | 18.00 | 54.9 | 54.2 | 56.7 | 55.3 | 1.3 | 34.84 |
| 16 | 1:40 | 8 | 2.00 | 69.7 | 70.0 | 69.8 | 69.8 | 0.2 | 36.88 |

TABLE 7

| | Factor | | | |
|---|---|---|---|---|
| Value name | Feedstock:MeOH molar ratio A | Catalyst loading B | Oleic acid loading C | Experimental error |
| $S_1$ | 138.4 | 115.3 | 139.0 | 132.9 |
| $S_2$ | 138.8 | 140.2 | 137.5 | 139.3 |
| $S_3$ | 136.0 | 142.4 | 134.6 | 136.3 |
| $S_4$ | 132.5 | 147.7 | 134.5 | 137.1 |
| $\overline{S_1}$ | 34.6 | 28.8 | 34.7 | — |
| $\overline{S_2}$ | 34.7 | 35.1 | 34.4 | — |
| $\overline{S_3}$ | 34.0 | 35.6 | 33.6 | — |
| $\overline{S_4}$ | 33.1 | 36.9 | 33.6 | — |
| max − min | 1.6 | 8.1 | 1.1 | — |

Figure 8:
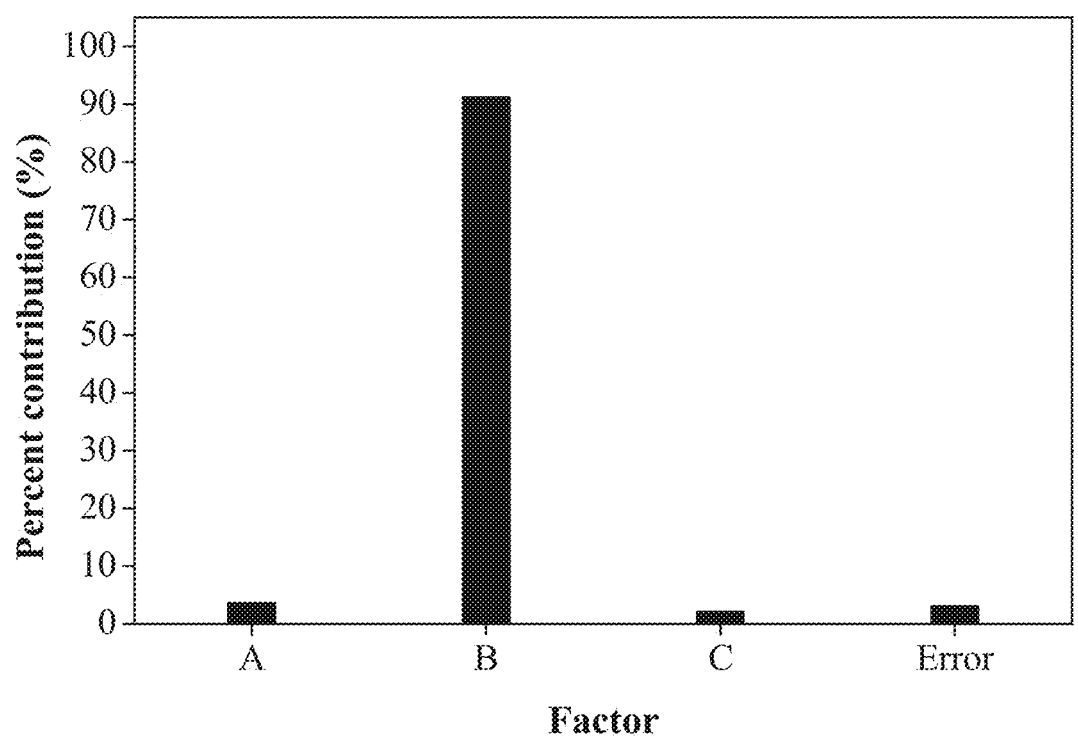
FIG. 8 shows the percentage of contribution from three factors to the catalytic reaction wherein factor A is feedstock:MeOH ratio, B is the catalyst loading, and C is the oleic acid loading.

The analysis of variance (ANOVA) was used as a statistical model to evaluate the whole optimization process under consideration of experimental error. At the 90% confidence level, $\alpha=0.1$, the critical F value ($F_\alpha$) can be found from the distribution table $F_{0.1}$ (2,2)=9.00. As tabulated in TABLE 8, it is obvious that $F_A$ (1.18)<$F_\alpha$; $F_B$ (29.92)>$F_\alpha$ and $F_C$ (0.70)<$F_\alpha$. The catalyst loading (factor B) is found to be the only prominent factor which contributes 91.24% to the overall catalytic conversion, followed by feedstock-to-methanol molar ratio (factor A, 3.59%) and oleic acid loading (factor C, 2.12%), as depicted in FIG. 8. The experimental error contributes to 3.05%, an indication that all the experimental results collected in this optimization process are reliable and no important factor is omitted.

TABLE 8

| Factor | $SS_j$ | $dF_j$ | $V_j$ | $F_j$ | $F_{0.1}$ (3,3) = 5.39 | $P_j$ (%) |
|---|---|---|---|---|---|---|
| A | 6.15 | 3 | 2.05 | 1.18 | < | 3.59 |
| B | 156.23 | 3 | 52.08 | 29.92 | > | 91.24 |
| C | 3.64 | 3 | 1.21 | 0.70 | < | 2.12 |
| Error | 5.22 | 3 | 1.74 | — | — | 3.05 |
| T | 171.24 | 12 | — | — | — | 100.00 |

Figure 9:
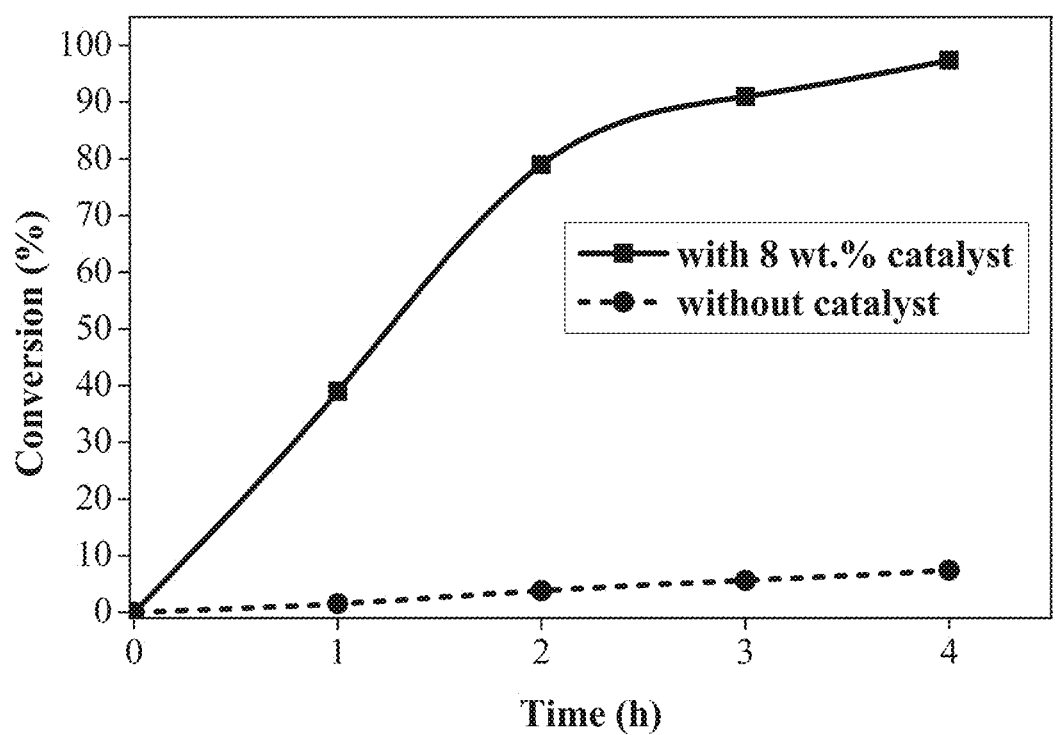
FIG. 9 shows the percentage of catalytic conversion within 4 hours with 8 wt. % catalyst and without.

As the catalytic conditions have been optimized, a time domain catalytic conversion profile of the $ZnFe_2O_4$ catalyzed simultaneous reaction under the optimal reaction conditions is depicted in FIG. 9. A remarkable catalytic conversion of 97.4% was achieved after 4 hours. A fast catalytic rate was clearly observed in the first two hours, and the rate started to slow down after 2 h. An equilibrium of the simultaneous reaction was reached at 4 h as the catalytic conversion was observed to level off. In contrast, a simultaneous reaction without the $ZnFe_2O_4$ catalyst achieved a conversion of only 7.4%.

Figure 10:
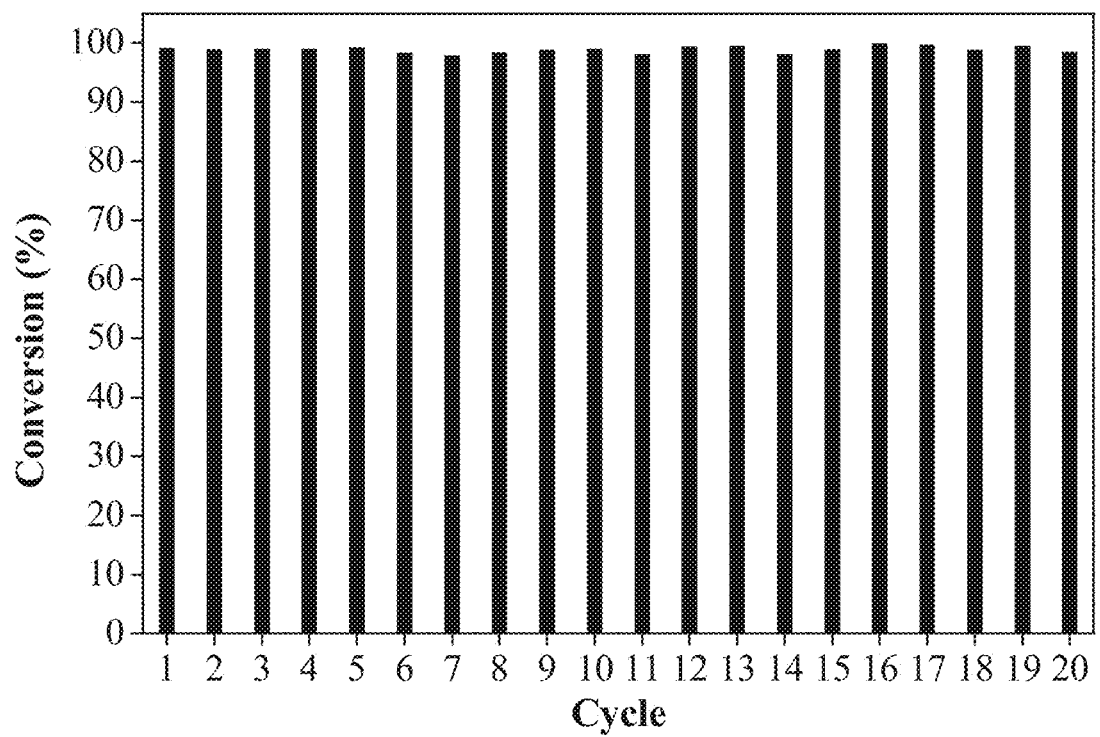
FIG. 10 shows the percentage of catalytic conversion for twenty catalytic cycles.

The introduction of heterogeneous catalyst for biodiesel production through a one-step simultaneous reaction is beneficial because of easier separation of final product from catalyst and minimization of environmental problems. Besides catalytic performance, recovery and durability are also important aspects to evaluate a heterogeneous catalyst. In the present invention, the $ZnFe_2O_4$ catalyst could be reused after regeneration without any further washing steps. The reusability of the $ZnFe_2O_4$ catalyst on the one-step simultaneous reaction was investigated, and the results were summarized in FIG. 10. The $ZnFe_2O_4$ catalyst demonstrated excellent durability and robustness for twenty catalytic cycles with conversion over 97.5%.

Figure 11:
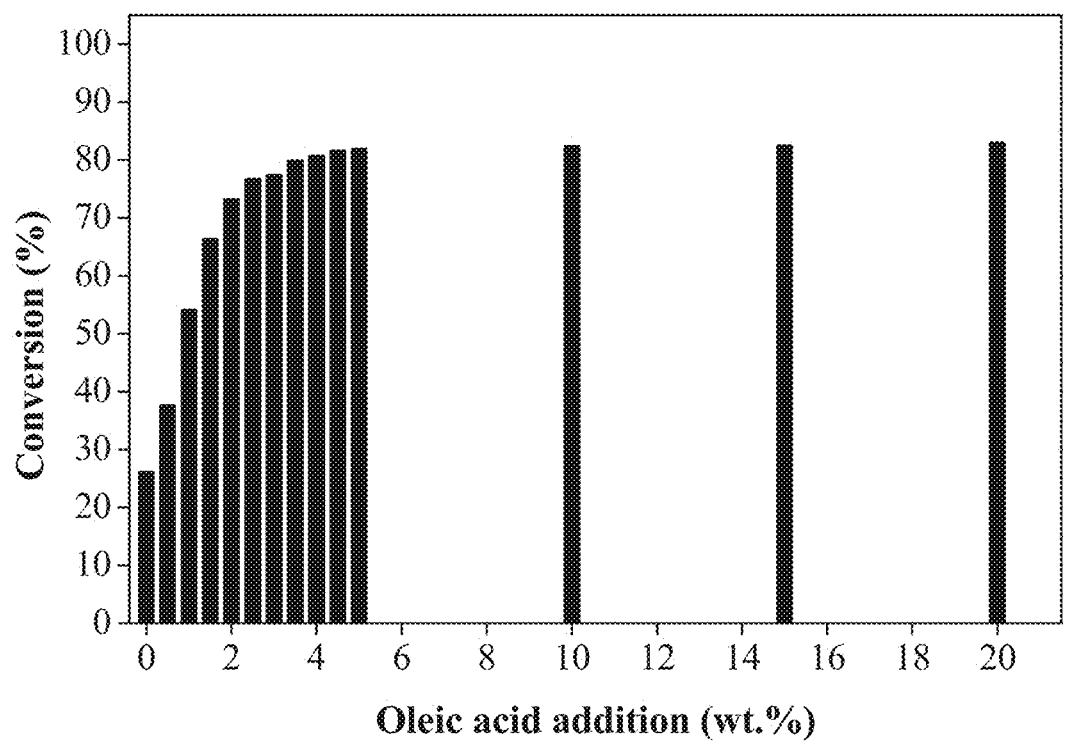
FIG. 11 shows the relationship between percentage of catalytic conversion and weight % of oleic acid.

According to the S/N ratio analysis, the $\overline{S_{Ci}}$ value suggests that the catalytic conversion is significantly influenced by the oleic acid content in feedstock especially in the lower oleic acid content (2.00 wt. %-18.00 wt. %). In order to investigate the effect of FFA content and the threshold FFA content that can significantly maximize the catalytic rate, different amounts of oleic acid were screened for the simultaneous reaction with the results summarized in FIG. 11. A gradual increase of the catalytic conversion from 26.0% to 73.1% was observed with an increase of oleic acid addition from 0.00 wt. % to 2.00 wt. %. Further increase of the oleic acid loading to 4.50 wt. % resulted in the catalytic conversion reaching the threshold loading point, and no significant enhancement of catalytic conversion was observed with further increase in the oleic acid loading to 20.00 wt. %. This implied that the reaction rate of the one-step simultaneous reaction could be enhanced by simply increasing the FFA content, and the $ZnFe_2O_4$ catalyst demonstrated a high degree of FFA tolerance with a threshold oleic acid loading of 4.5 wt. % which maximized the catalytic rate.

In summary, the present catalyst differs from previously reported zinc ferrite. For example, when compared to the catalyst described in References 6 and 7, the present catalyst shows the differences summarized in TABLE 9.

TABLE 9

| Physiochemical Characteristic | Present catalyst | Catalyst from References 6 and 7 |
|---|---|---|
| Particle size | 34.5 ± 0.2 nm | Not provided |
| Crystalline size | 27.5 nm | 32 nm |
| Average grain size | 25.9 nm | Not provided |
| Surface area | 39.2 m$^2$/g | 12 m$^2$/g |
| Pore volume | 0.24 ml/g | 0.10 ml/g |
| Average pore size | 2 nm | 21 nm |
| Chemical identity | No free $Fe_2O_3$ found | Free $Fe_2O_3$ found |
| XPS | Zn2p$_{3/2}$ = 1022.0 eV | Zn2p$_{3/2}$ = 1021.4 eV |
| | O$_{lat}$ = 530.6 eV | O$_{lat}$ = 530 eV |
| | O$_{—OH}$ = 531.9 eV | O$_{—OH}$ = 532.2 eV |

The differences result from the present preparation protocol. Consequently, the present catalyst is more active since it leads to higher conversion at lower temperature (100-140° C. versus 180° C.) in shorter reaction time.

REFERENCES

1. S. Yan, S. O. Salley and K. Y. S. Ng. Methods and catalysts for making biodiesel from the transesterification and esterification of unrefined oils. U.S. Pat. No. 8,163,946.
2. R. Stern, G. Hillion, J. J. Rouxel and S. Leporq. Process for the production of esters from vegetable oils or animal oils alcohols. U.S. Pat. No. 5,908,946.
3. H. W. Li, P. M. Lu, W. Luo, Z. M. Wang, F. Yan, L. M. Yang and Z. H. Yuan. Fe (II)-Zn solid acid catalyst for synthesizing biodiesel and preparation method. CN patent application 101811055.
4. P. S. Sreeprasanth, R. Srivastava, D. Srinivas and P. Ratnasamy. Hydrophobic, solid acid catalysts for production of biofuels and lubricants. Appl. Catal. A: Gen, 2006, 314, 148-159.
5. F. Yan, Z. H. Yuan, P. M. Lu, W. Luo, L. M. Yang and L. Deng. Fe—Zn double-metal cyanide complexes catalyzed biodiesel production from high-acid-value oil. Renew. Energy, 2011, 36, 2026-2031.
6. K. Thirunavukkarasu, T. M. Sankaranarayanan, A. Pandurangan, R. Vijaya Shanthi and S. Sivasanker. The role of surface $Zn^{2+}$ ions in the transesterification of vegetable oils over ZnO supported on $Al_2O_3$ supported on $Al_2O_3$ and $Fe_2O_3$. Catal. Sci. Technol., 2014, 4, 851-860.
7. T. M. Sankaranarayanan, R. Vijaya Shanthi, K. Thirunavukkarasu, A. Pandurangan and S. Sivasanker. Catalytic properties of spinel-type mixed oxides in transesterification of vegetable oils. J. Mol. Catal. A: Chem., 2013, 379, 234-242.

What is claimed is:

1. A method for preparing a sulfur-free $ZnFe_2O_4$ catalyst, comprising the steps of:
   a. preparing a first solution by dissolving ethylenediaminetetraacetic acid (EDTA) in purified water, followed by adding a base until the pH is 3 to 10;
   b. preparing a second solution by dissolving a surfactant in purified water;
   c. adding the second solution dropwise to the first solution;
   d. preparing a third solution by dissolving a zinc salt and an iron (III) salt in purified water;
   e. adding the third solution dropwise into the solution resulting from step (c);
   f. drying the solution resulting from step (e) to form a dried mixed metal EDTA complex;
   g. calcining said dried mixed metal EDTA complex in air to obtain said $ZnFe_2O_4$ catalyst.

2. The method of claim 1, wherein said base is selected from the group consisting of ammonia water ($NH_4OH$), potassium hydroxide (KOH) and sodium hydroxide (NaOH).

3. The method of claim 1, wherein said surfactant is selected from the group consisting of polyvinylpyrrolidone (PVP), polyvinyl alcohol (PVA), poly(acrylic acid) (PAA), poly(malic acid), poly(acrylic acid-co-malic acid), poly(ethyleneimine) (PEI), ethylene glycol (EG), polyethylene glycol (PEG) and polyethylene glycol tert-octylphenyl ether.

4. The method of claim 1, wherein said surfactant has an average molecular weight of 400 to 55000.

5. The method of claim 1, wherein said zinc salt is selected from the group consisting of zinc nitrate hexahydrate ($Zn(NO_3)_2.6H_2O$), zinc chloride ($ZnCl_2$), zinc sulphate heptahydrate ($ZnSO_4.7H_2O$), zinc oxalate ($ZnC_2O_4$), zinc acetate dihydrate ($Zn(CH_3COO)_2.2H_2O$), zinc citrate dihydrate (($C_6H_5O_7)_2Zn_3.2H_2O$), zinc oxide (ZnO), zinc hydroxide ($Zn(OH)_2$), zinc carbonate ($ZnCO_3$) and zinc carbonate basic ($[ZnCO_3]_2.[Zn(OH)_2]_3$).

6. The method of claim 1, wherein said iron (III) salt is selected from the group consisting of iron (II) nitrate ($Fe(NO_3)_2$), iron (III) nitrate nonahydrate ($Fe(NO_3)_3.9H_2O$), iron (II) chloride tetrahydrate ($FeCl_2.4H_2O$), iron (III) chloride hexahydrate ($FeCl_3.6H_2O$), iron (II) sulphate heptahydrate ($FeSO_4.7H_2O$), iron (III) sulphate ($Fe_2(SO_4)_3$), iron (II) oxalate dihydrate ($FeC_2O_4.2H_2O$), iron (III) oxalate hexahydrate ($Fe_2(C_2O_4)_3.6H_2O$), iron (II) acetate ($Fe(CH_3COO)_2$), iron (III) citrate ($C_6H_5O_7Fe$), iron (II) oxide (FeO), iron (III) oxide ($Fe_2O_3$), iron (II) hydroxide ($Fe(OH)_2$), iron (III) hydroxide ($Fe(OH)_3$), iron (II) carbonate ($FeCO_3$), iron (III) carbonate ($Fe_2(CO_3)_3$) and iron oxide hydroxide (FeOOH).

7. The method of claim 1, wherein said mixed metal EDTA complex is calcined at a temperature ranging from 300° C. to 700° C.

8. A method for transesterification, comprising the steps of:
   a. providing a sulfur-free $ZnFe_2O_4$ catalyst;
   b. contacting said catalyst with one or more alcohols and a composition comprising one or more esters to form a reaction mixture; and
   c. heating said reaction mixture to form transesterification products.

9. The method of claim 8, wherein said one or more esters are triglycerides, wherein the fatty acid portions of said triglycerides are selected from the group consisting of acetic acid, propanoic acid, butanoic acid, pentanoic acid, hexanoic acid, heptanoic acid, octanoic acid, nonanoic acid, capric acid, undecanoic acid, lauric acid, tridecanoic acid, myristic acid, myristoleic acid, pentadecanoic acid, palmitic acid, palmitoleic acid, sapienic acid, heptadecanoic acid, stearic acid, oleic acid, elaidic acid, vaccenic acid, petroselinic acid, linoleic acid, linolelaidic acid, linolenic acid, stearidonic acid, nonadecanoic acid, eicosanoic acid, gadoleic acid, gondoic acid, paullinic acid, dihomo-γ-linolenic acid, mead acid, arachidonic acid, eicosapentaenoic acid, heneicosanoic acid, behenic acid, erucic acid, adrenic acid, docosahexaenoic acid, tricosanoic acid, lignoceric acid, nervonic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, ceroplastic acid, hexatriacontanoic acid, heptatriacontanoic acid and octatriacontanoic acid.

10. The method of claim 8, wherein said one or more alcohols are selected from the group consisting of methanol, ethanol, propanol, butanol, pentanol, hexanol, heptanol, octanol, nonanol, decanol and the isomers thereof.

11. The method of claim 8, wherein said composition comprising one or more esters is a biodiesel feedstock.

12. The method of claim 8, wherein said composition further comprises one or more free fatty acids selected from the group consisting of acetic acid, propanoic acid, butanoic acid, pentanoic acid, hexanoic acid, heptanoic acid, octanoic acid, nonanoic acid, capric acid, undecanoic acid, lauric acid, tridecanoic acid, myristic acid, myristoleic acid, pentadecanoic acid, palmitic acid, palmitoleic acid, sapienic acid, heptadecanoic acid, stearic acid, oleic acid, elaidic acid, vaccenic acid, petroselinic acid, linoleic acid, linolelaidic acid, linolenic acid, stearidonic acid, nonadecanoic acid, eicosanoic acid, gadoleic acid, gondoic acid, paullinic acid, dihomo-γ-linolenic acid, mead acid, arachidonic acid, eicosapentaenoic acid, heneicosanoic acid, behenic acid, erucic acid, adrenic acid, docosahexaenoic acid, tricosanoic acid, lignoceric acid, nervonic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, ceroplastic acid, hexatriacontanoic acid, heptatriacontanoic acid and octatriacontanoic acid for enhancing the reaction rate and conversion of said one or more esters.

13. The method of claim 12, wherein said one or more free fatty acids make up at least 0.5 wt % of said composition.

14. The method of claim 12, wherein the number of moles of said one or more alcohols is at least six times the total number of moles of both said one or more esters and said one or more fatty acids.

15. The method of claim 8, wherein said reaction mixture is heated at a temperature ranging from 100° C. to 300° C.

16. The method of claim 8, wherein said reaction mixture comprises 2 wt % to 8 wt % of $ZnFe_2O_4$.

17. A catalyst for catalyzing the esterification of fatty acids or transesterification of esters, comprising sulfur-free $ZnFe_2O_4$ spinel nanoparticles, wherein said $ZnFe_2O_4$ has a surface area ranging from 20 $m^2$/g to 100 $m^2$/g.

18. The catalyst of claim 17, wherein said $ZnFe_2O_4$ has a particle size ranging from 30 nm to 60 nm.

19. The catalyst of claim 17, wherein said $ZnFe_2O_4$ has a pore volume ranging from 0.1 ml/g to 0.6 ml/g.

20. The catalyst of claim 17, wherein said $ZnFe_2O_4$ has an average pore size ranging from 1 nm to 15 nm.

* * * * *